(12) United States Patent
Dirghangi et al.

(10) Patent No.: US 10,687,705 B2
(45) Date of Patent: Jun. 23, 2020

(54) METHOD FOR AUTOMATING COLLECTION, ASSOCIATION, AND COORDINATION OF MULTIPLE MEDICAL DATA SOURCES

(71) Applicant: Scanoptix, Inc., Charlottesville, VA (US)

(72) Inventors: Arjun Dirghangi, Charlottesville, VA (US); Dustin Williams, Bothell, WA (US); Jeffrey Iris, Sammamish, WA (US); Ayush Sagar, Somerville, MA (US)

(73) Assignee: Scanoptix, Inc., Charlottesville, VA (US)

( * ) Notice: Subject to any disclaimer, the term of this patent is extended or adjusted under 35 U.S.C. 154(b) by 0 days.

(21) Appl. No.: 16/459,552

(22) Filed: Jul. 1, 2019

(65) Prior Publication Data
US 2019/0320898 A1 Oct. 24, 2019

Related U.S. Application Data

(63) Continuation of application No. 15/892,286, filed on Feb. 8, 2018, now Pat. No. 10,376,142.

(60) Provisional application No. 62/456,630, filed on Feb. 8, 2017.

(51) Int. Cl.
| | |
|---|---|
| A61B 3/18 | (2006.01) |
| A61B 3/14 | (2006.01) |
| A61B 3/00 | (2006.01) |
| A61B 3/13 | (2006.01) |

(Continued)

(52) U.S. Cl.
CPC .............. *A61B 3/185* (2013.01); *A61B 3/005* (2013.01); *A61B 3/0025* (2013.01); *A61B 3/0033* (2013.01); *A61B 3/12* (2013.01); *A61B 3/132* (2013.01); *A61B 3/145* (2013.01);

(Continued)

(58) Field of Classification Search
CPC ....... A61B 3/185; A61B 3/0025; A61B 3/005; A61B 3/12; A61B 3/0033; A61B 3/156; A61B 3/145; A61B 2560/0475; A61B 2560/045; A61B 3/15; A61B 3/132
See application file for complete search history.

(56) References Cited

U.S. PATENT DOCUMENTS

| | | | |
|---|---|---|---|
| 2004/0122790 A1 | 6/2004 | Walker et al. | |
| 2016/0004820 A1 | 1/2016 | Moore | |

OTHER PUBLICATIONS

PCT/US2019/040209 Search Report and Written Opinion (10 pages).

*Primary Examiner* — Jack Dinh
(74) *Attorney, Agent, or Firm* — Wood Rogers PLC; Nathan A. Evans

(57) ABSTRACT

A method of automating the collection, association, and coordination of multiple medical data sources using a coordinating service application, computer, database, and/or server system to manage devices, examinations, and people involved in the medical examination and treatment process. In an embodiment, the method comprises authenticating a user for a premises, a device, or a device group, validating particular use of the device based on user credentials or type of device or device group, associating a medical examination with a patient or a medical examination schedule, associating medical examination data from a device or device group with a related medical examination session, routing medical examination data to a computer, database, or server, and pairing medical examination session data with a medical interpretation, clinical testing results, diagnoses, and/or other recorded information.

24 Claims, 12 Drawing Sheets

(51) Int. Cl.
*A61B 3/12* (2006.01)
*A61B 3/15* (2006.01)
(52) U.S. Cl.
CPC ............... *A61B 3/15* (2013.01); *A61B 3/156* (2013.01); *A61B 2560/045* (2013.01); *A61B 2560/0475* (2013.01)

METHOD FOR AUTOMATING COLLECTION, ASSOCIATION, AND COORDINATION OF MULTIPLE MEDICAL DATA SOURCES

CROSS-REFERENCE TO RELATED APPLICATIONS

The present application relies on the disclosures of and claims priority to and the benefit of the filing date of U.S. Provisional Application No. 62/456,630, filed Feb. 8, 2017. This application is a continuation-in-part of U.S. application Ser. No. 15/892,286 filed Feb. 8, 2018. The disclosures of those applications are hereby incorporated by reference herein in their entireties.

BACKGROUND

Field of the Invention

The present invention is directed to a medical data network system and method of capturing, coordinating, linking, organizing, storing, and/or communicating between one or more connected health workers or devices using a system of electronic sensors, computational devices, and networked antennas embedded—in one embodiment into or onto clinical equipment and medical instruments—in an edge computing model to direct on-device computational processing power, special sensing capabilities, and networked off-device storage and remote processing. In embodiments, the system and method is, in part, to directly extend and augment the capabilities of connected health workers beyond the traditional paradigm of separate medical instruments, personal mobile computing devices, and independently located computer terminals into an interconnected, connected examination room, in which the capacity to record clinical data, refer to independent electronic data sets in separate databases, and algorithmically track and predict the activities and needs of clinicians is embedded directly into the tools used by connected health workers on a regular basis, minimizing the need for manual processes and user-unfriendly, inefficient keyboard-and-mouse user interfaces for routine computational tasks in clinical medicine. The system and method allow for the capabilities of special sensing, data linking, cross-referencing, and algorithmic analysis of patient-related data, which may be shared with clinicians and health workers. This type of coordination would ordinarily would be either impossible or extremely onerous to perform. By using an edge computing model directly embedding networked computational power into the medical devices used routinely in clinical settings, multiple use cases and clinical decision making tools can be enabled algorithmically which, by linking diverse data types in real- or close to real-time, are not currently possible or available to clinicians and health workers simultaneously within their daily clinical workflows. Use of this technology allows for the automation of medical device management, capture of clinical practice-related data, and generation of medical documentation and billing- and coding-related reports with, in aspects, one set of compatible electronic medical devices capable of automatically generating networks of medical devices that are capable of linking basic demographic and financial patient-related data with location-, physician- and allied health worker-related authentication and data audit trail-, type of device-, scheduling- and time-based, examination type-, and patient exam-related data.

Description of Related Art

Multiple clinical, administrative, business, maintenance and support, clinical research, and clinical engineering staff are required to do only a subset of the above described processes, which often require special, ad hoc, project undertaking to achieve complex tasks such as: tracking and optimizing bottlenecks in clinical workflows; monitoring and addressing clinical device maintenance and inventory tasks; tracking patient and staff location-based movements within clinical spaces and steps of clinical encounters; and determining medical risks for individual patients based upon linking medical examination-related findings cross-referencing physical findings with demographic, medication use, and other health record-based data. In addition to the inherent inefficiencies in current practices to achieve such goals (which in practice means most such information is usually unknown or known only in limited or distorted ways), existing limitations in linking diverse and difficult-to-link data types in clinical practice means that many of the most salient insights into clinical practice management and examination of each patient are de facto not possible. Additionally, these types of manual processes inherently miss data intrinsic to the current, in-progress clinical examination by the doctor and have to be manually associated with clinical documentation generated by the physician for the specific clinical encounter in question (or imported into a linked entry into the electronic medical record). Limitations in physicians and ancillary staff availability and time to accomplish more than the minimum activities key to clinical care, as well as increasing documentation burdens instituted by medicolegal concerns, insurance payer requirements, and profound inefficiencies inherent in conventional keyboard- and mouse-based user interfaces of conventional electronic health record software systems, render most such activities de facto currently impossible during routine clinical activities.

Additionally, detailed insights regarding medical device usage and clinical process activities are currently difficult or impossible to obtain using conventional techniques. By linking patient medical histories with algorithmic deep learning approaches to image classification systems, researchers have found previously unknown biomarkers for diseases like Alzheimer's dementia from fundus photographs (images of the retina and optic nerves of patients). However, these algorithmic processes are at present not linked to the daily workflows of clinicians and practice personnel, and as such, the entry and registration of patient-related history and physical data, the collection of examination-related data such as patient imaging, and the computational processing, analysis, and reporting of findings often require multiple personnel, different physical locations required for patient movement within the clinical encounter, and data capture and analysis occurring asynchronously from the place and time that the examining physician or allied health worker would actually be examining and treating the patient.

As such, collecting and analyzing such additional data types require additional staff, with analytical reports generated and available at another time (usually after) than the treating physician is actually seeing the patient, and often after the patient has left the medical office or hospital setting. Usually, such reports can only be generated ad hoc as part of either dedicated clinical research or quality improvement projects, and usually require dedicated data science personnel and software to collect and analyze such data, with often manual retrieval and association of various data types required in order to generate the analysis. Additionally, indirect or ad hoc approaches must be taken to infer and indirectly measure metrics relevant to clinical activities due to the inability to routinely directly capture the said clinical activities in real time given the sorts of technological and staffing limitations in the current clinical standard of care previously discussed. In practice, this leads to profound inefficiencies and a clinical workflow of data collection and analysis which is de-linked from the actual process of the medical encounter. The examining physician, in this example, does not have additional information needed from such novel algorithms or medical devices during their patient encounter, when the data could be most useful, and will need to resort to other strategies such as calling the patient back for a discussion of findings once the analysis of additional data is made available to them. Finally, the actual practice of collecting, linking, and organizing such data and then making medical decisions based upon what the analysis may entail often creates a host of additional clerical and user interface-related processes that creates an added burden for the treating physician which further serves to distance, distract, and slow down their clinical workflow and presents additional demands on their time either within or after the medical encounter. It also represents additional "screen time" not addressing the patient during the medical encounter, when it is preferable to both physician and patient to instead maximize "face time" during the medical encounter.

SUMMARY OF THE INVENTION

The system and method taught herein constitutes an electronic connection, in aspects, between medical devices, physicians, and/or patients or patient data with a paired "hub" system to manage devices (the "spokes" in a hub-and-spoke analogy), examinations, and people (e.g., physicians and patients) involved in the examination process. The hub comprises, in aspects, a processor (e.g., a CPU) or coordinating service application and associated computing processes, wirelessly connected to a device(s) or an examiner(s) in or around an examining facility, such as a doctor's office or hospital setting, to monitor activity and permit multiple device control and coordination. In one aspect, for example, the hub will receive images and data/information from a device taught herein (e.g., an ophthalmoscope) or other devices (including, but not limited to, mobile and networked embedded systems in which medical devices and instruments have compatible networked microprocessor/microcontroller, device software, and operating system embedded into their physical makeup or by the use of hardware adapters to achieve the same goals), and the hub will be used, along with uniquely identifiable markers such as, but not limited to, hardware tokens, bar- or QR-codes, identification cards, encoded magnetic or solid-state electronic memory cards and/or compatible wireless antennas and solid state computing chips to detect and manage the hierarchy of trusted users engaged in use of a connected network of devices to perform tasks from administrative organization tasks to improvement of medical examination. The system, in aspects, authenticates and correlates users seeking to use the system and associated devices with patients and their associated examination sessions to link users with devices, patients, and examination sessions and to maintain an associated audit trail of user access and usage of protected health information. The system also reviews and analyzes the data obtained from an examination, manages the data for storage, syncs images and data from an examination (e.g., fundus photos with diagnoses), processes images or information, and/or manages remote data synchronization and/or local or remote data and imagery (including, but no limited to, still- or video images) redisplay. It may manage storing such information locally or remotely, such as in the cloud. (See, e.g., FIG. 1.)

BRIEF DESCRIPTION OF THE DRAWINGS

The accompanying drawings illustrate certain aspects of some of the embodiments of the present invention, and should not be used to limit or define the invention. Together with the written description the drawings serve to explain certain principles of the invention.

DETAILED DESCRIPTION OF VARIOUS EMBODIMENTS OF THE INVENTION

Figure 1:
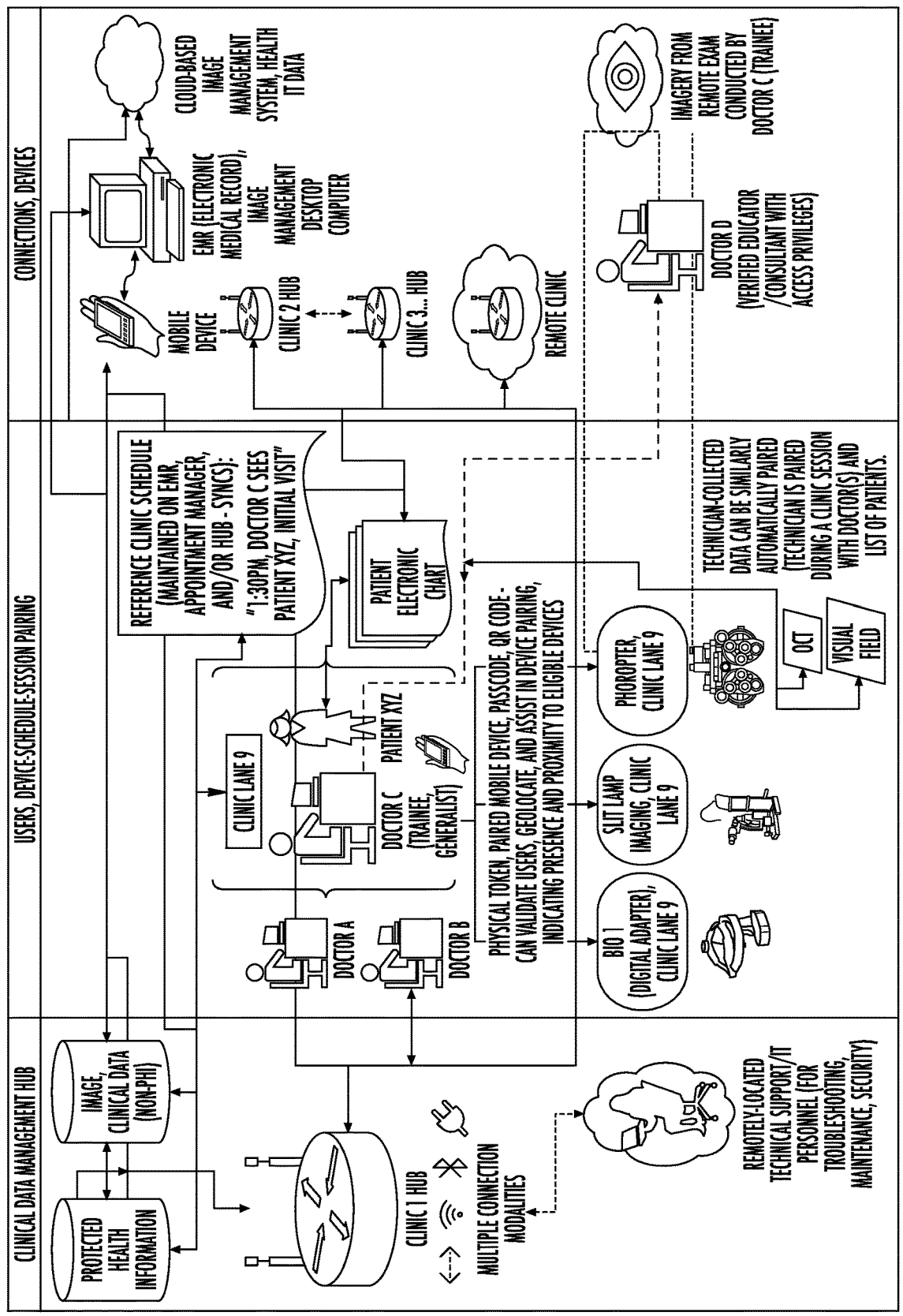
FIG. 1 is a block diagram of conceptual relationships between a remote monitoring station and its use in managing data flows between multiple devices and multiple users according to an embodiment.

The present invention has been described with reference to particular embodiments having various features. It will be apparent to those skilled in the art that various modifications and variations can be made in the practice of the present invention without departing from the scope or spirit of the invention. One skilled in the art will recognize that these features may be used singularly or in any combination based on the requirements and specifications of a given application or design. Embodiments comprising various features may also consist of or consist essentially of those various features. Other embodiments of the invention will be apparent to those skilled in the art from consideration of the specification and practice of the invention. The description of the invention provided is merely exemplary in nature and, thus, variations that do not depart from the essence of the invention are intended to be within the scope of the invention. All references cited in this specification are hereby incorporated by reference in their entireties.

By using a clinical data network which can, with minimal user interaction: recognize the treating physician, recognize the patient and scheduled time of the encounter, collect data using the clinical tools already used by physicians and their staff, recognize compatible equipment and their physical location, correlate the collected examination data with patient history, and generate clinical- and billing-related documentation, the physician and health personnel are freed to focus upon clinical-related tasks, not clerical- and administrative-related tasks. This generates greater practice efficiencies as well as increased patient, staff, and physician satisfaction. The physician can focus upon the patient and clinical examination, with a set of novel examination-related clinical associations and data reports available within the clinical encounter itself, rather than at a separate time, maximizing the utility of and what is possible to be done during the medical examination time.

Clinical scenarios and processes made possible by this technology, include but are not limited to:

Synchronizing, backing up data onto local memory and/or cloud storage (currently requires multiple processes and often multiple staff members to manually enter demographic information, export and import data between multiple computer and software systems);

Filing and queuing images for storage, subsequent remote data synchronization, or redisplay and review of data and still- and/or video imagery (currently requires manual generation of lists of data-capture tasks such as Modality Worklist to inform staff about which image capture, registration, filing, and backup tasks need to be done);

Synchronizing data between multiple stations, which also requires a similar set of processes and cannot capture examination-related data or clinical documentation; and Redisplaying data, which usually requires manual data export or additional wired cabling and bulky additional equipment which presents a host of usability challenges within the often limited space of the clinical encounter.

In certain instances such as smaller private practice clinics, dedicated information technology administration personnel may not be available and it may be more desirable for device administration, storage, and computational processing to be primarily located off-device, remotely, via electronic networked remote systems, also known as in the cloud. Additionally, using cloud storage and processing allows for increased capabilities in advanced algorithmic analysis such as deep learning of clinical images and linked health datasets, and computer vision-based automatic analysis of clinical imagery captured during the physician's examination process, as well as machine learning for predictive practice analytics of phenomena such as predicted clinical volumes of patient and testing flows to better match scheduling and staffing at particular times for a physician's clinic based upon past behavior. In other clinical settings, Internet and network connectivity may be less reliable, or from an information security perspective, network administrators may prefer that connected medical devices, storage, and processing occur only on a local area network. Connection to an AC-powered (as opposed to battery-powered) power source, for example, could enable a greater amount of on-device processing, whereas in a battery-powered mode, the system would offload more computationally- and power-intensive processes to remote servers (cloud processing), to maximize battery life during wireless device usage.

The current invention describes a system architecture capable of nimbly adjusting between more, or less, on-device and local processing, and adjusting between local network instances of the system software, and remote/cloud-connected network connectivity which requires a connection to the Internet, allowing a single, flexible system to be deployed in a diverse array of clinical settings and adjusted to various network deployment scenarios with a minimum of manual reconfiguration. A clinic-wide network can be fully self-contained, or securely connected via electronic networks to external networks (intranet as well as Internet).

The current invention describes tagging, or association, of clinical data obtained via compatible devices, correlating timestamps, user, and location of the device(s) with a clinical schedule for a clinic, hospital, clinical area and/or specialty, provider/physician, location, etc. As such, the invention describes the automatic referencing and association of captured clinical data with a set of clinic schedules which can automatically associate captured data with a specific treating physician, location, and patient. (See, e.g., FIG. 1.)

The system can allow for wired or wireless connections in between the various compatible devices as well as the clinical data management hub.

A variety of techniques can be used to maintain data security, data integrity, reduce exposure to inadvertent protected health information disclosure, and maintain a data access audit trail to maintain health information security and compliance with appropriate health data security standards such as HIPAA and the U.S. HITECH Act. Data can be isolated in independent repositories based upon their level of sensitivity, such that protected health information (PHI) may be located in a separate database (and possibly location) than non-PHI. Additional techniques such as on-device encryption, encryption of data in transit and at rest, and blockchain technologies, may also be used.

In aspects, the current invention encompasses the following:

Facilitating automatic hierarchical connections between detected trusted team members and linked connected instruments/diagnostics (see, e.g., FIGS. 2-3, 6, 11-12);

Context-aware computing (of both users and tools), such as automated detecting of what user needs so that display, redisplay, and other information relayed to practitioner (for example) is tailored to practitioner's needs, reduces burden of manual data entry by physicians and support staff, reduces inefficiencies in what user reviews and/or inputs, and reduces medical errors;

Recognizing and coding device-specific data types, integrating data into EMR/EHR with user, patient, and device metadata (for example, a specific diagnostic instrument being detected to be used by a user (e.g., ophthalmoscope by an ophthalmologist) in Clinic Lane 9 for Patient XYZ, wherein the system automatically designates and configures the other compatible devices (e.g., slit lamp and phoropter) in Clinic Lane 9 as being available and with data entered for the same patient session (see e.g., FIG. 1));

Utilizing multi-device, multi-user control (e.g., multiple devices can be used by multiple users in multiple different ways (including the associated data and/or metadata)) (see, FIG. 1);

Calculating clinical device usage metrics and workflow analytics, enabling improved clinic management by generating information specific to that user (such as a physician) and his or her patients and staff regarding patient and staff flows and practice bottlenecks in real-time, or in close to real-time or at a later time, or in automated interactive reports generated using system data;

Device- and user-specific data tagging validates point-of-care automated billing, by being able to validate the user, the patient, the organ or system being examined or intervened upon, the device being used, and the procedure performed, cross-referenced against the time of the procedure and various diagnoses ascribed to the patient, which could be presented via local or remote data display to the physician for validation using a compatible device (such as, in one aspect, pressing a device key which is interpreted by the system to indicate validation or rejection of the clinical results data and documentation being presented) in real-time or close to real-time, or at a later time, in order to automatically generate authenticated documentation for coding and billing clinical diagnostic tests and clinical procedures, which would be securely validated by the physician or a designee and would enable the billing and coding documentation to be electronically sent automatically to the physician's business and coding departments for submission to insurance companies or other payers (see, e.g., FIG. 1);

Remote server hub and local embedded client technology integrated into medical devices and instruments, cross-referenced against databases and entered information regarding physical location and proximity to other compatible instruments and devices allows for automatic, remotely pushed device updates and to home in on points of failure, for remote troubleshooting and maintenance of connected medical equipment (see, e.g., FIGS. 1-6, 10-12; and/or Using physical tokens, sensors (such as RFID sensors), virtual and/or software-based tokens and virtual medical devices, passcodes, QR codes, and/or bar codes can be used to validate users and/or geolocate devices and users, and assist in device pairing and validation of clinical activities/processes (such as conducting a procedure, dilating a patient, or verifying that transcribed documentation or automatically suggested analytical data is correct). In aspects, these tokens or codes, for example, can also be used to indicate presence and proximity of authenticated user(s) and eligible device(s). (See, e.g., FIG. 1.)

In embodiments, the system can synchronize to and reference a master schedule or set of associated scheduling data for a particular clinician, set of workers, clinical area, or specialty, and given the time of day and authenticated user using a device or set of devices and the physical location of the devices being used, can retrieve a list of eligible patients who are likely to have had the tests or procedures possible given the data generated by the devices used. For example, the data may indicate and/or determine: at 1:30 pm, Doctor C sees Patient XYZ in Exam Room 9, Initial Visit. Thus, data collected at 1:30 pm compatible with an initial visit examination in Room 9 would result in a narrowed list of potential patients from the clinic schedule, which could then be retrieved and displayed to the physician and/or health worker such as administrative personnel or a technician to verify and associate the specific patient's demographic details (such as name, date of birth, and medical record number) with the clinical data obtained during that clinical encounter. Accordingly, the system could provide "ground truth" as to which patient had which procedures, done when, by which personnel, and in which area, which in turn, may be used to authenticate and produce clinically verified medical documentation suitable for the electronic health/medical record as well as for billing and coding purposes. (See, e.g., FIGS. 1, 8.)

The reverse process can also be used—such that by referencing with a clinic schedule for a specific clinician, that clinician, once authenticated (either using a passcode or a physical token), when entering Room 9, the system could automatically have one or more devices (pre-determined to be used routinely in an initial visit for that physician) made ready for the physician to use and configured to accept data for a specific patient for a specific clinical encounter (medical examination session) and export data and/or metadata to that patient's medical record, as well as an output or input associated with the session such as a medical interpretation, diagnosis, results (such as lab, diagnostic testing, imaging, and/or pathology results) without additional physician manual intervention. (See, e.g., FIGS. 1-5, 11-12.)

Technician-collected data can be similarly automatically paired (technician or allied health worker(s) such as a nurse is paired during a clinic session with doctor(s) and list of patients) to allow automatic data entry, validation, documentation, and association with the appropriate medical record(s), which can be of particular benefit in situations in which multiple patients and doctors may have various tasks completed at various stages by multiple technicians (potentially with varying levels of privileges to conduct various clinical activities), and to allow simultaneous tracking and dashboard generation of reports regarding staffing workflows, practice efficiencies, and algorithmic forecasting of staff requirements based upon past task-based needs of individual clinics, patient types, clinic schedules, and individual staff performance. (See, e.g., FIGS. 1-5, 11-12.) Similarly, the system would allow the automatic generation of a report documenting that, in one aspect, Technician A performed dilation task for Patient X at 10:30 am, or that at 2:47 pm, Ultrasound Technologist B performed a W ultrasound procedure for N organ system(s), which correlates to cross-referenced diagnosis in the patient's medical record of Z Syndrome, which correlates to a reimbursement amount of $Y in a lookup table of W ultrasound procedure billing for a diagnosis of Z. Such documentation could be provided for redisplay by the system automatically and interactively to the billing provider (physician in this example) for validation step, with the billing provider's credentials time-stamped, authenticated, and entered in the associated documentation for automatic transmission to the associated Billing and Coding department or business office. In certain embodiments, different arrangements and combinations of automatic authentication, collection, and documentation of clinical data capture can be generated, with similar documentation generated and presented for validation by the billing and/or attending/senior physician or practitioner, while minimizing manual data entry and manipulation tasks by clinicians and staff.

In embodiments, the invention allows for remotely-located technical support/IT personnel (for troubleshooting, maintenance, security, etc. of the system and associated devices), given that metadata message types for each device are passed back to the data management hub routinely offering information regarding device status, and the system can be configured to allow for remote configuration, management, maintenance, upgrading, and disabling of device software. An interface can be displayed either locally, on a remote server or client, showing device status of one or more eligible devices to be maintained by an administrator of pre-determined privileges. An example of this may be an interface to display battery health status of all eligible devices in a hospital, or an interface to automatically display devices with anomalous data or malfunctioning status to aid an administrator in allocating clinical engineering resources more intelligently in a just-in-time fashion, rather than (and a substantial advancement upon) the existing practices of making sweeps by dedicated clinical or engineering personnel at predetermined intervals, manually checking the status of all medical devices in a specific area, which is both time-consuming, inefficient, and will necessarily miss newly-malfunctioning devices in between such set intervals unless a user calls clinical engineering or technical support personnel to call in the issue, which can result in malfunctioning equipment impacting clinical examinations or patients directly. (See, e.g., FIGS. 1-3.) Also, by using digital adapter technology to be coupled or affixed to existing medical equipment and tools, the system will allow conventional "manual" medical instruments and devices (not connected to any networked computational processing or electronic storage) to be transformed into "smart" electronically networked devices, which can be recognized and managed just as natively electronic devices with embedded onboard networked computing might be by the system here taught. Additionally, the system can allow notifications of various types (such as malfunctioning compatible equipment) to be sent to external sources such as e-mail, text messages, or smartphone applications to more conveniently alert administrators.

Data from devices connected to the system may be forwarded via electronic networks to be redisplayed to remotely located personnel, such as verified teaching physicians/consultants with access privileges.

In an educational example, Doctor D (a verified educator/consultant with access privileges) may use the system to review, addend, and verify data and documentation generated via connected devices conducted from a remote examination, conducted by Doctor C (a trainee). (See, e.g., FIG. 1.)

Multiple clinical locations, location types, and physical locations can be linked electronically via securely-connected electronic networks, allowing for care and coordination of clinical data between one or more clinical settings, local as well as remote clinics, as well as a variety of inpatient and outpatient clinical settings, including surgery centers.

In one aspect, auto analysis will occur using connected software to correlate clinical images with an external library or set of algorithms determining attributes such as, in an ophthalmic setting, which eye is being examined, or flagging optic nerve and retinal periphery, noting abnormal features detected by the system, all of which aid in clinical examination upon review of the image(s). Auto analysis may also enable redisplaying image flags or algorithmically/computationally-generated metadata in multiple formats, such as, but not limited to, text or annotated images and video. In one embodiment, auto analysis can display its output by electronically transmitting metadata and clinical imagery to a connected EMR/EHR (Electronic Medical Record/Electronic Health Record) system or a separate connected computing device or application linked to a patient's electronic chart. In another embodiment, redisplay of auto analysis results can be accomplished by superimposing automatically-generated tags and/or graphical overlays illustrating areas of concern upon the captured imagery. Using pre- or post-image processing, the images taken during the examination process or generated from video capture, will automatically join photographs capturing adjacent regions of the fundus, synthesizing a montage map of the patient's fundus automatically with minimal or no user intervention, enabling cross-comparison of images between patient examinations and between patients. Such cross-comparison can also be conducted, in one embodiment, by quick point-of-care cross-reference to a normative or pathologic database of fundus imagery (still or video) to enable immediate or close to immediate reference of patient pathology to an external image library for augmented examination enabling substantially enhanced clinical utility of the dilated fundus examination by the use of augmented examination technology. This will make the examination shorter and more comfortable to the patient, while permitting the practitioner a longer time to subsequently study the fundus by and through the images captured by the device and integrated system.

The device also incorporates security features to maintain patient confidentiality, system integrity, and integration of the device, integrated system, and other connected devices into an existing secure information technology network for use in a clinical setting. Videos/images/clinical metadata/ and any other telemetry/data may be encrypted by the device, allowing for secure transmission of data to a trusted (previously approved, and having undergone appropriate credentialing processes for a set of authorized clinical activities in a particular clinical setting or settings) user or group of users and allowing for a hierarchical data trail to be generated for access and manipulation of clinical data. Physical tokens, passcodes, or connected trusted devices can be used, with or without the use of a connected off-device remote monitoring station, or "hub," to automatically detect the presence, absence, and/or use of the system by a user with access privileges, or trusted team member (e.g., a verified user with data access privileges), and appropriately tag and file generated imagery and metadata with a hierarchical audit trail to maintain data integrity, automate the appropriate tagging and filing of generated clinical imagery and documentation, and maintain clinical data in compliance with relevant regulatory protocols for protected health information, as well as for clinical research data applications. In the context of this network, "trust" or "trusted" generally means securely paired or previously established/verified user or device with data access privileges. (See, e.g., FIGS. 1, 3-4, 6, 11-12.)

In one preferred embodiment, the embedded microprocessor and wireless antenna array, along with integrated, secure remote networking software such as VPN software along with algorithmic techniques such as packet forwarding, will allow trusted system technicians to troubleshoot, maintain, and update the device or groups of devices and integrated system remotely and provide automatic periodic updates to enhance system stability, security, and enable automatic rollout of new software-enabled functions and enhanced functionality of the paired devices and/or digital adapter systems over time. (See, e.g., FIG. 1.)

Machine learning/automated image element recognition for the system may also be included as part of the device and/or system. Such technology may be used to, for example in an ophthalmic setting, recognize that a focused retina is in view (such as, in aspects, to initiate capture, or to flag a captured image with a "high quality" metadata tag), to recognize which eye is examined, and when a higher zoom is used or needed (for example, to capture the optic nerve head of each eye), to locate large library/libraries of tagged fundus images (e.g., R/L) for algorithmic computer vision-based fundus photography image grading using computing applications and algorithms, and/or rapidly collect large datasets of clinical imagery alone or in combination with clinical metadata for artificial intelligence-based healthcare automation software systems.

Figure 9:
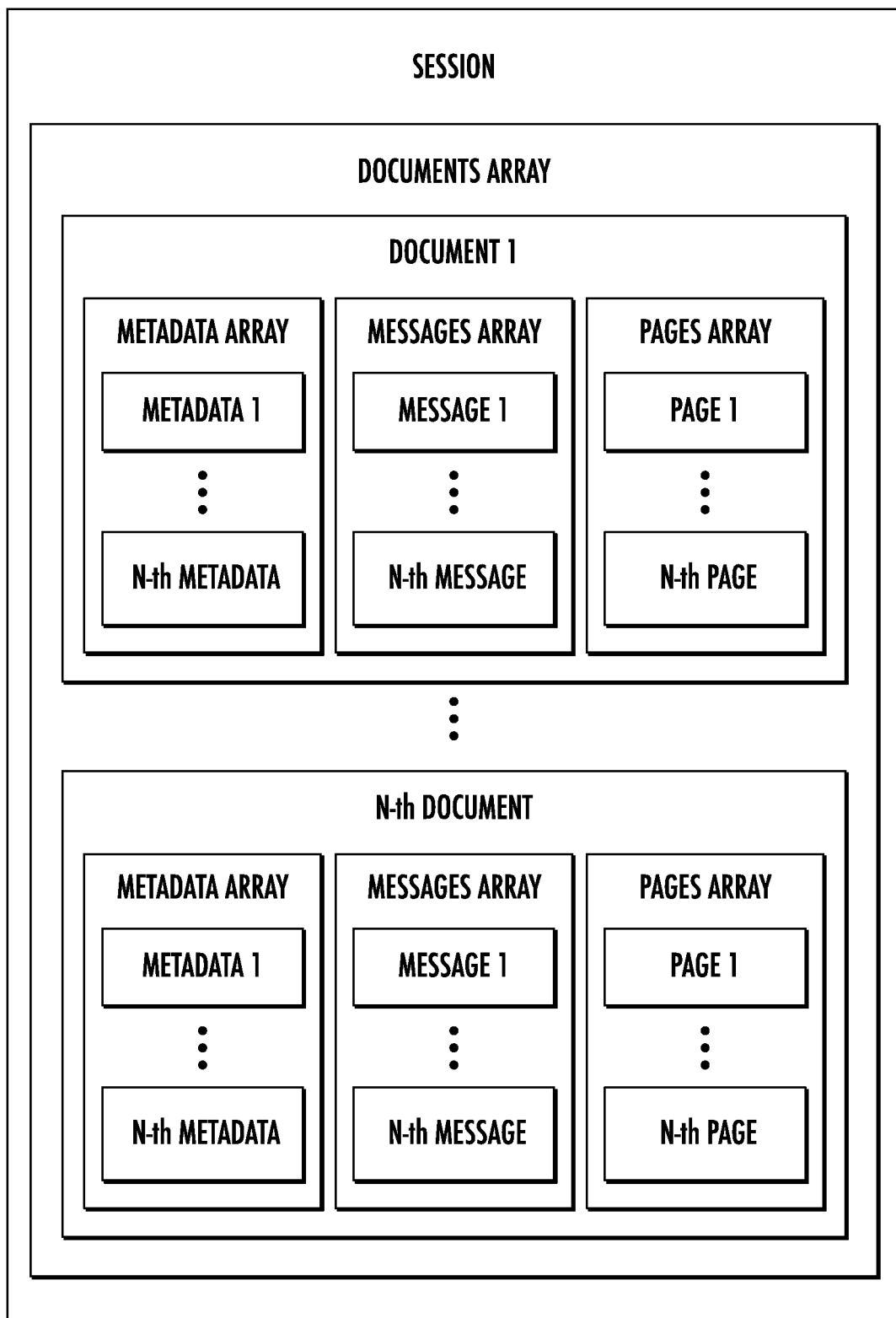
FIG. 9 is a block diagram illustrating a relationship between Session, Document, and Page according to an embodiment.

Regarding data formats, data that is created and stored by the device is referred to as, in some aspects, a document. (See FIG. 9.) A document may contain multiple blocks of data received from the hardware device. These blocks of data are referred to as pages. (See FIG. 9.) A document must contain at least one page, but has no upper limit on the number of pages. An exception to this is if there are errors on the device. In that case, a document with no pages can be returned, but the error collection will be filled in. Also, if there are errors, the document may still contain pages. However, these pages should be assumed to represent invalid data. Documents are grouped together in a session, which generally represents a patient exam. (See FIG. 9.) Sessions may contain documents obtained from multiple different hardware devices. Each session, document, and page within the documents may have searchable metadata that is not patient identifiable. This is to provide a quick means of searching without having to decrypt every record.

In one aspect, the basic structure may appear as follows. A session may, in one example but not limited to this, comprise: Identification number; Medical Record Number/MRN (Unicode String), which, in preferred embodiments, is encrypted, or the real value is stored elsewhere and a hash is used; Start Timestamp (DateTime) Unix Epoch Time (ms since Jan. 1, 1970); End Timestamp (DateTime) Unix Epoch Time (ms since Jan. 1, 1970); ResponsibleParties (Array); Location (Unicode String); and/or Documents (Array). A document may, in one example, comprise: Identification (such as a unique identifier); Session Identification; Device or Device Group Identification; Operator, User, or Patient Identification; Date or Metadata (Array); Pages (Array); and/or Messages (Array). A page may, in one example, comprise: Identification (Globally Unique Identifier); Document Identification; Data Type Description (blood pressure, fundus image, etc.) (Unicode String); Data Format (image/jpeg, audio/mp3, plain/text, etc.) (Unicode String); Timestamp (DateTime) Unix Epoch Time (ms since Jan. 1, 1970); Metadata (Array); and/or Data (Byte Array), in a preferred embodiment stored in a different database to keep actual patient data separate from identifying data. A message may, in one example, comprise: Identification; Document Identification; Device or Device Group Message Id (Nullable INT); Severity (enum of byte); MessageType (enum of INT16); and/or Text (Unicode String). Metadata may, in one example, comprise: Identification; Key (Unicode String); and/or Value (Unicode String).

The system and method taught herein may also be used as part of or in electronic connection with a paired "hub" to manage devices, examinations, and people involved in the examination process. In aspects, the hub may comprise a processor (e.g., a CPU) or a coordinating service application, a host of remote or local servers, a centralized server, or a distributed cloud service, and may be connected to the Internet with wire(s) or wirelessly. It may also be unconnected from the Internet and/or local networks. In a preferred embodiment, the hub will be wirelessly connected to device(s) or device groups or examiner(s)/user(s) in or around the examining facility/premises to monitor activity and permit multiple device or device group control and coordination. In one aspect, the hub will receive images and data/information/metadata from the device or device group taught herein or other devices. The hub may receive results/output, such as a patient diagnosis. Results may also be lab, diagnostic testing, imaging, and/or pathology results. The hub may receive medical interpretation information. Medical interpretation includes, but is not limited to, a critical analysis of patient data in order to assist with medical decision-making. It will be used, along with uniquely identifiable markers such as hardware tokens, physical tokens, paired mobile devices, and/or passcodes, to detect and manage the hierarchy of trusted users engaged in use of a connected network of devices or device groups as previously described. It will process the data, review the data, analyze the data, manage for storage, synchronize data/metadata/audio files/text files/simple or rich text/images (including still and video imagery) and information, process images or information, and/or manage remote data synchronization and/or local or remote redisplay. It may also manage storing such information locally or remotely.

For example, the hub may be connected to several devices or device groups taught herein within a facility/premises. The hub will record when such devices or device groups are being used and who is using the devices or device groups, as described above. The hub will log, save, organize, and process such information in order to, among other things, know when examinations were/are being performed, what kind of examinations were/are being performed, and who was/is performing such examinations. Personnel in or around the facility may be tracked, in one aspect, by having an Radio Frequency Identification ("RFID") device on their person, or by tracking a cell phone or some other device wirelessly, the position which can, in one aspect, be triangulated in relation to wireless antennas with known position(s), or in another aspect, be determined by time-of-flight estimation in relation to antennas located onboard various devices with known locations in the clinical environment, or by other location techniques. The information collected by the hub may be cross-referenced with other information, for example a reference schedule, to track activity in or around the facility. In another example, the hub may automatically, or with user input, pair patient data/imagery and metadata collected during a medical examination with the specific patient and associated doctor/user at that appointment time (e.g., medical examination session), with the hub subsequently associating and exporting collected data to the patient's EMR/EHR based on the reference clinical schedule used. (See, e.g., FIGS. 1-6, 8, 10-12.)

Now turning to the Figures more specifically, FIG. 1 is a block diagram of conceptual relationships between the remote monitoring station and its use in managing data flows between the multiple devices and multiple users, including:
Syncing, backing up data onto local memory and/or cloud storage;
Filing and queuing data/metadata/images for storage, subsequent remote syncing, or redisplay of data;
In aspects, using AC power source to offload more power- and computationally-intensive off-device post-processing (such as computer vision-based auto-analysis);
Using master and child reference schedule-based automated metadata tagging of medical data with patients by location, user, and/or timestamp;
Having clinic-wide network be fully self-contained or securely connected to external networks (Intranet and/or Internet);
Using variety of techniques to maintain security, data integrity, reduce exposure to inadvertent protected patient health information ("PHI") disclosure, and maintain data access audit trail, such as independent data silos of PHI & non-PHI;
Using, in aspects, on-device encryption and/or blockchain;
Facilitating automatic hierarchical connections between detected trusted team members/users, linked connected instruments/diagnostics (e.g., devices or device groups);

Computing with context-aware computing (of both users and tools/devices/device groups), which reduces burden of manual data entry by physicians and support staff, and reduces medical errors;

Recognizing and coding device-specific data types, integrating data into EMR/EHR with user, patient, and device metadata;

Enabling multi-device, multi-user control;

Calculating clinical device usage metrics and workflow analytics, enabling improved clinic management in real-time/close to real-time or in automated output reports; and/or Enabling device- and user-specific data tagging, which validates point-of-care automated billing, and can be used for automatic device updates and to home in on points of failure, for remote troubleshooting and maintenance of connected medical equipment.

Figure 2:
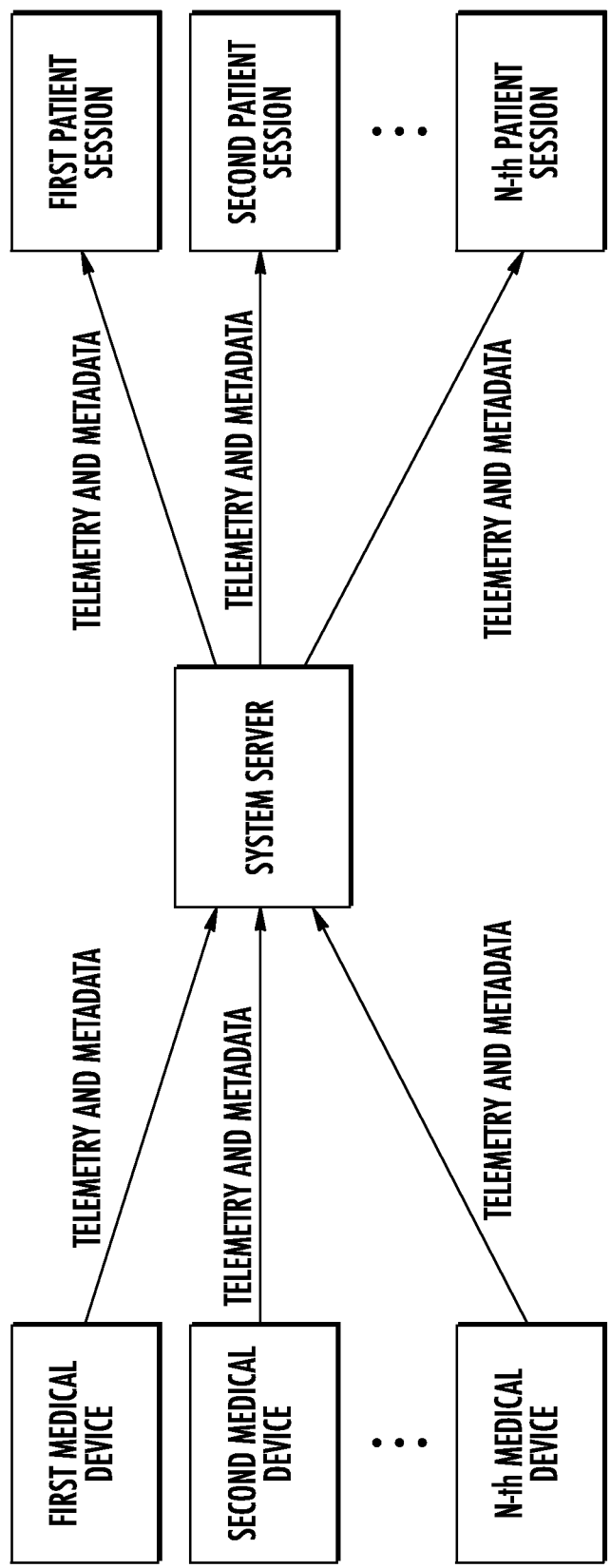
FIG. 2 is a block diagram displaying data, such as telemetry and metadata, being transmitted from medical devices or device groups to a centralized System Server via, in examples, a coordinating service application, according to an embodiment. The System Server may route and associate the received data to appropriate patient sessions according to an embodiment.

FIG. 2 is a flowchart of a "Document" workflow according to the present invention. FIG. 2 shows Session, Document, and Page relationships in a conceptual diagram of the data relationships within the system. The blocks of the block diagram represent parent-child relationships between the data objects. Data that is contained within a set or array is indicated by the '1 to Nth' notation and a vertical ellipsis.

Figure 3:
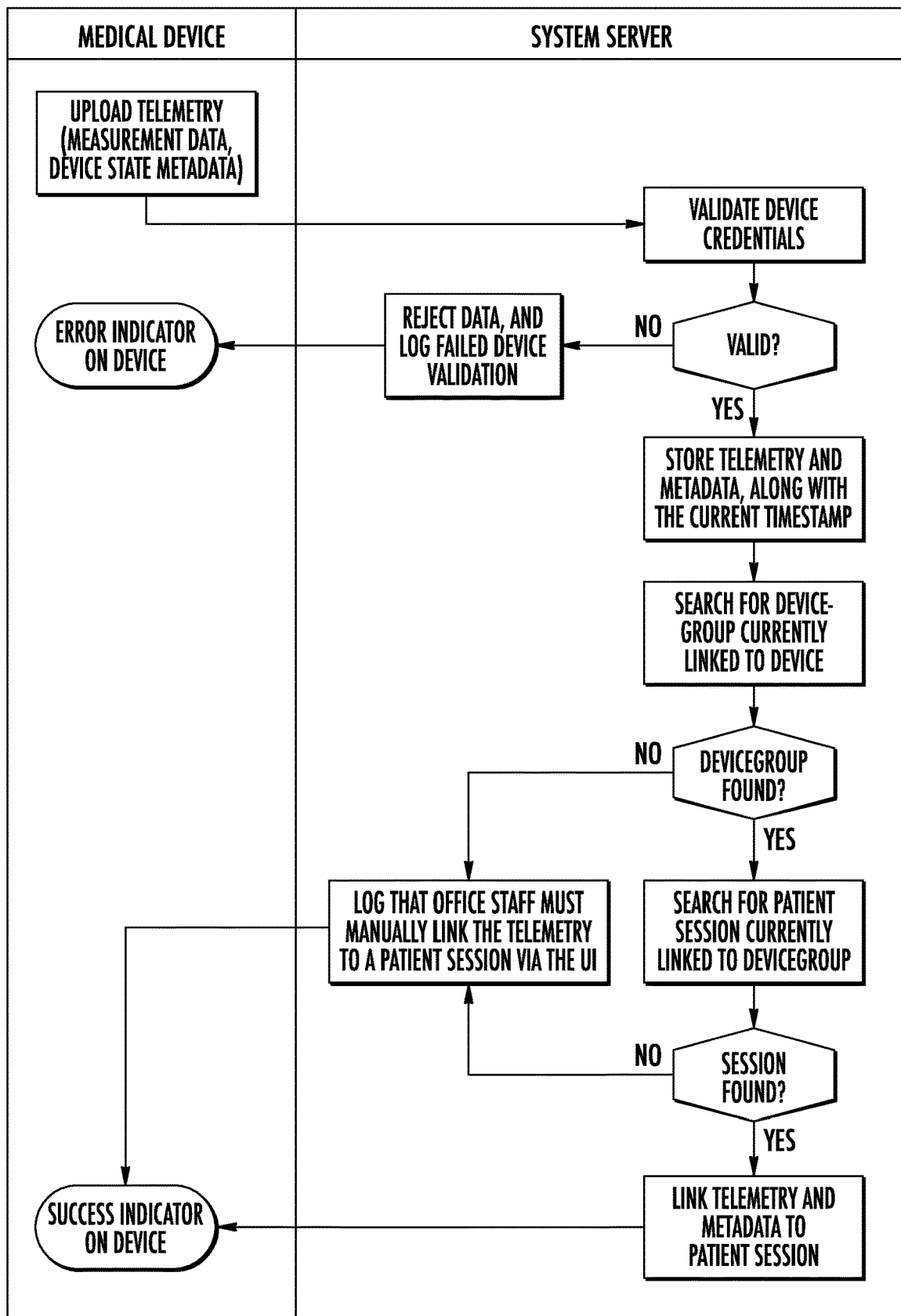
FIG. 3 is a flowchart showing a workflow and medical telemetry and metadata upload according to an embodiment.

FIG. 3 also shows the process by which a Device links to a DeviceGroup. It further shows the process by which a DeviceGroup links to Patient Session, and shows the process by which a user would link an existing DeviceGroup to a patient's Session. This link establishes the route by which uploaded data/metadata from Devices is sent to a patient's Session and is essential for automatic processing of uploaded data, metadata, output, results, diagnosis, and/or telemetry.

Figure 4:
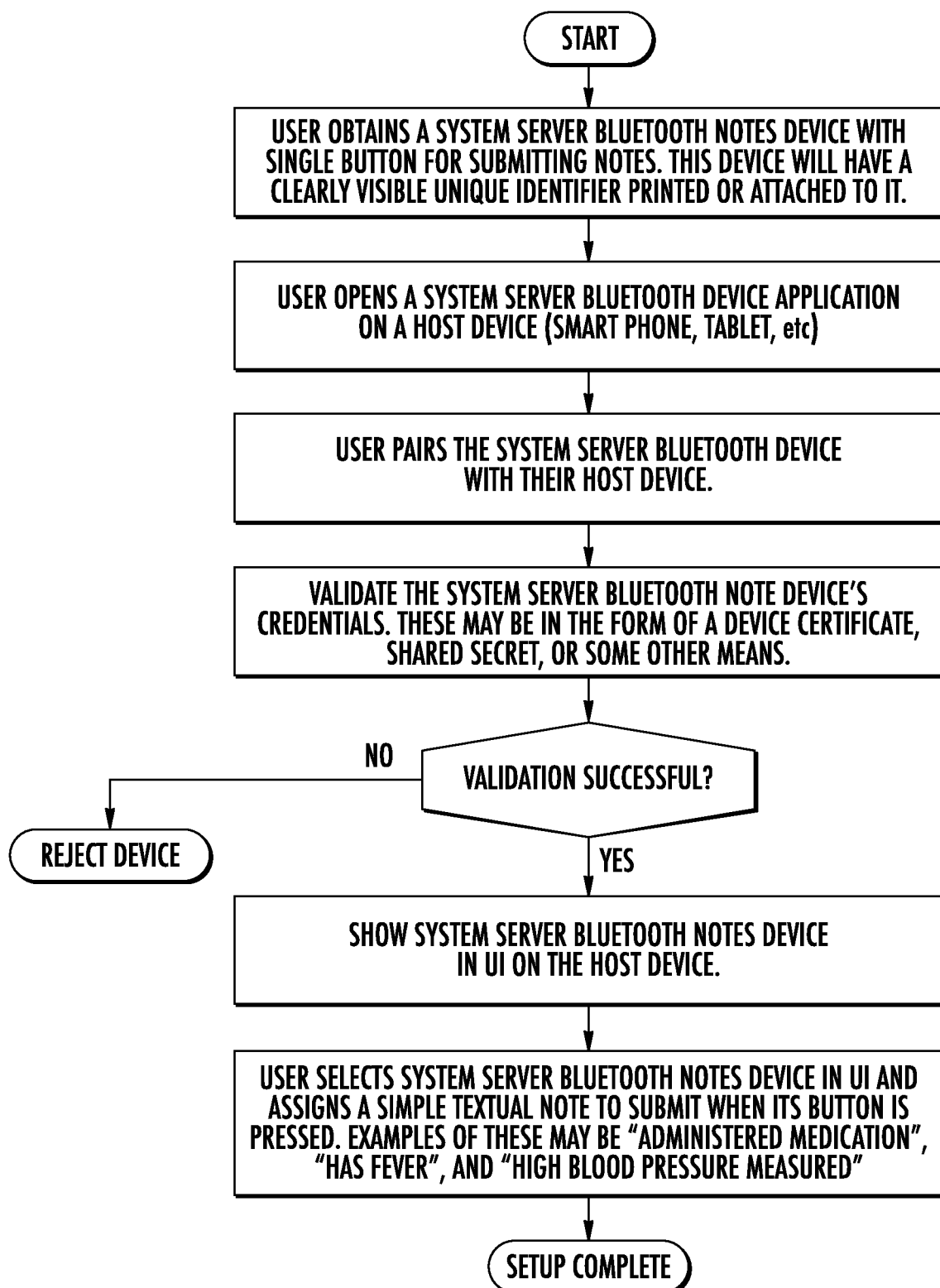
FIG. 4 is a flowchart illustrating a method of authenticating a device and setting up Bluetooth Button Note Device according to an embodiment.

FIG. 4 shows Bluetooth button virtual device functionality. On a virtual device, a user can specify a predefined Document to submit and link the submission of the Document to a Bluetooth button that is paired with a host device. FIG. 4 also shows the setup of Bluetooth button note devices. The host device, in aspects, has a software based virtual device that responds to the user pressing the Bluetooth button, and sends the predefined Document associated with that Bluetooth button to the remote system.

Figure 5:
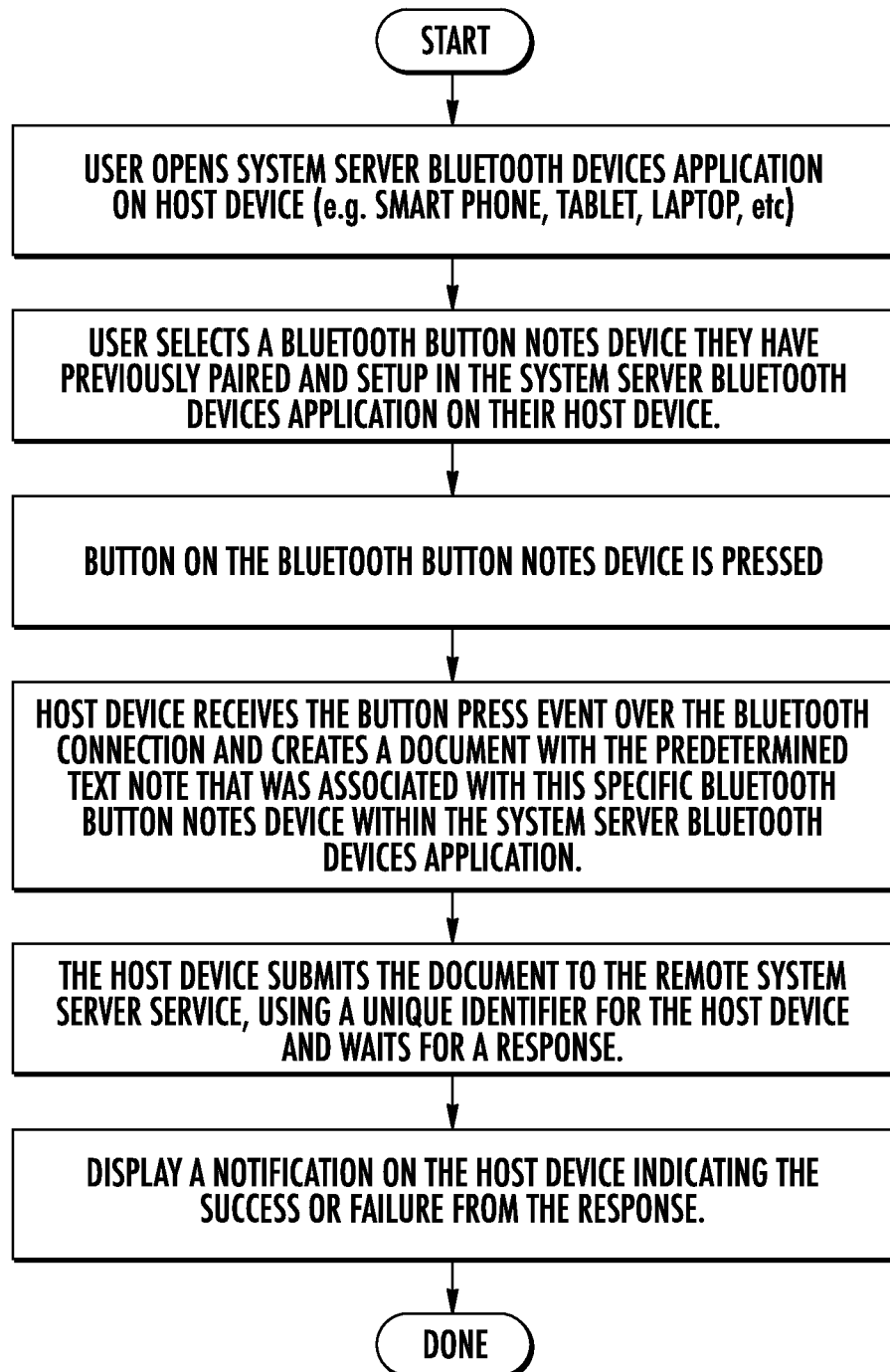
FIG. 5 is a flowchart illustrating a method of submitting notes according to an embodiment.

FIG. 5 illustrates submitting notes via Bluetooth notes devices. A novel use of the Bluetooth button note virtual device is to allow a user to carry a set of small Bluetooth buttons on a key chain, by way of example, or other external and/or mobile electronic device, and quickly submit notes as the user interacts with the patient. The user would, in aspects, log into the patient's Session via a smart badge reader or other secure physical or virtual device, and this would associate a special "personal" DeviceGroup linked to the user. These virtual devices would be associated with this special "personal" DeviceGroup, and note Documents submitted by the virtual devices would automatically be routed to the patient's Session. This would also allow the host device to automatically create a Document with a predetermined text note associated with the function of the specific note device within the system server Bluetooth devices application.

Figure 6:
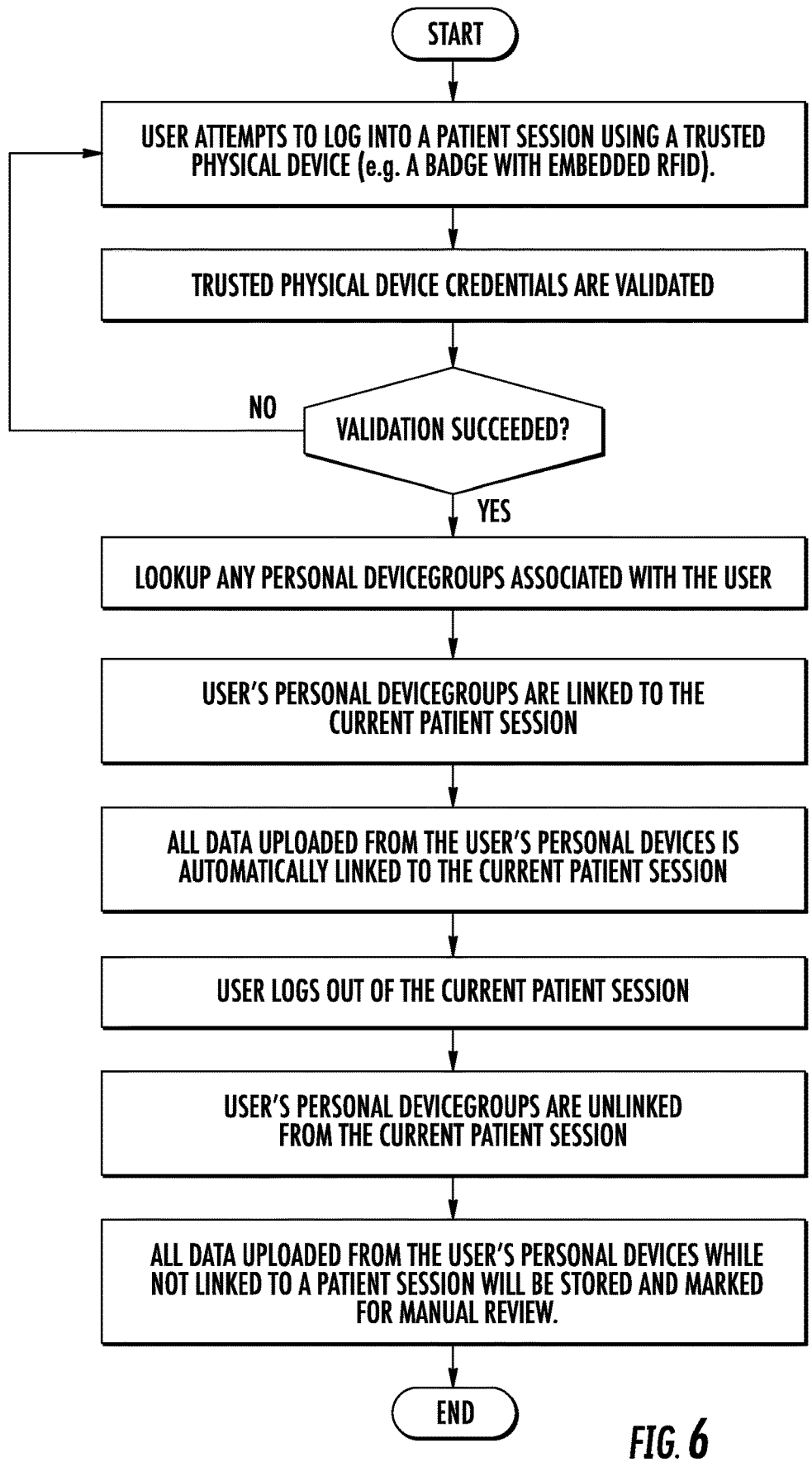
FIG. 6 is a flowchart illustrating a method of linking a device or device group to a session according to an embodiment.
Figure 12:
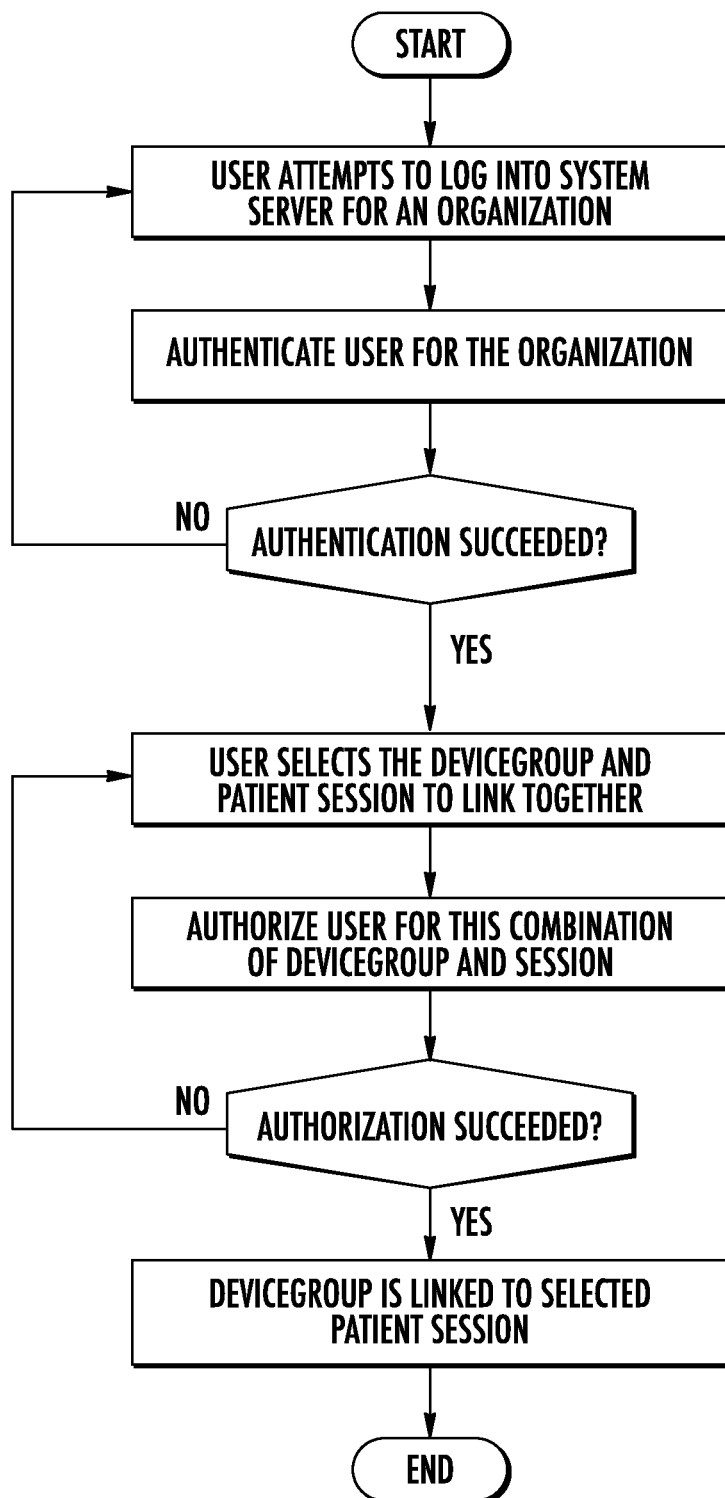
FIG. 12 is a flowchart illustrating a method of user authentication and linking a device or device group to a medical examination session according to an embodiment.

FIG. 6 shows auto linking a user's device or device group to Session (i.e., a medical examination session). It also shows the authentication process validating the user via a trusted physical device, such as a token, badge, RFID, etc. Further, in FIG. 11, the flowchart shows the process by which a user would link a device to a device group according to an embodiment. In FIG. 12, a flowchart illustrates the process by which a user links a device group to a medical examination session. This link establishes the route by which uploaded data/metadata from devices is sent to a patient medical examination session and is essential for automatic processing of uploaded data.

Figure 7:
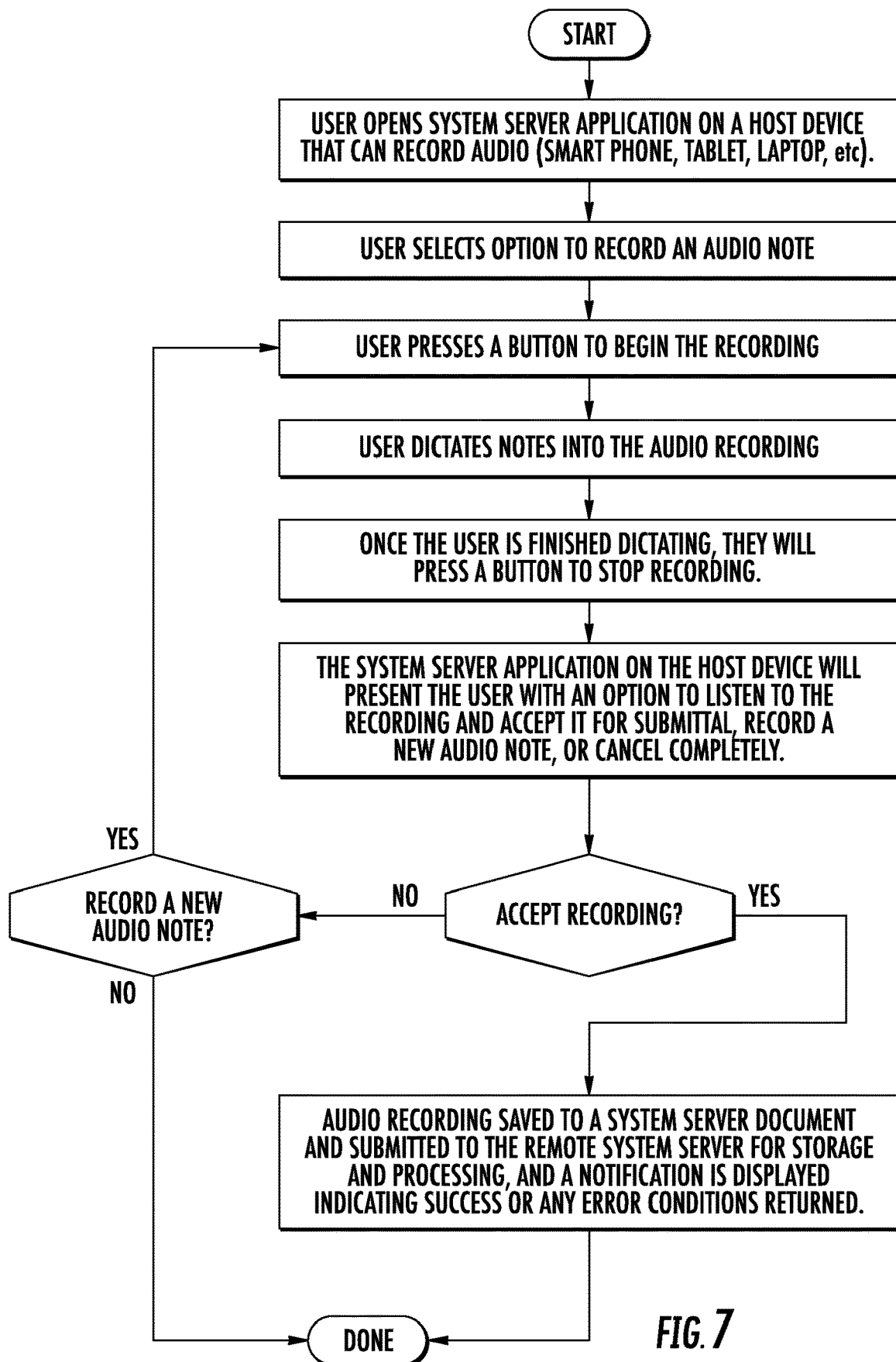
FIG. 7 is a flowchart illustrating a method of submitting audio notes according to an embodiment.

FIG. 7 shows an audio note dictation virtual device, which allows the user to dictate an audio note, review it, and submit it as a Document to a Session. This virtual device relies on a host device to provide audio capture capabilities, and is a purely software based virtual device. A host device launches a small application to record the audio note and allow the user to review it, and accept or reject it. Accepting it will convert the audio note into a Document to submit to the remote system and link to the current patient's Session by the normal means (e.g., via Device and DeviceGroup links to the Session). FIG. 7 also shows an audio note dictation virtual device, which allows the user to dictate an audio note, review it, and submit it as a Document to a Session. This virtual device relies on a host device to provide audio capture capabilities, and is a purely software based virtual device. A host device launches a small application to record the audio note and allow the user to review it, and accept or reject it. Accepting it will convert the audio note into a Document to submit to the remote system and link to the current patient's Session by the normal means (e.g., via Device and DeviceGroup links to the Session).

Figure 8:
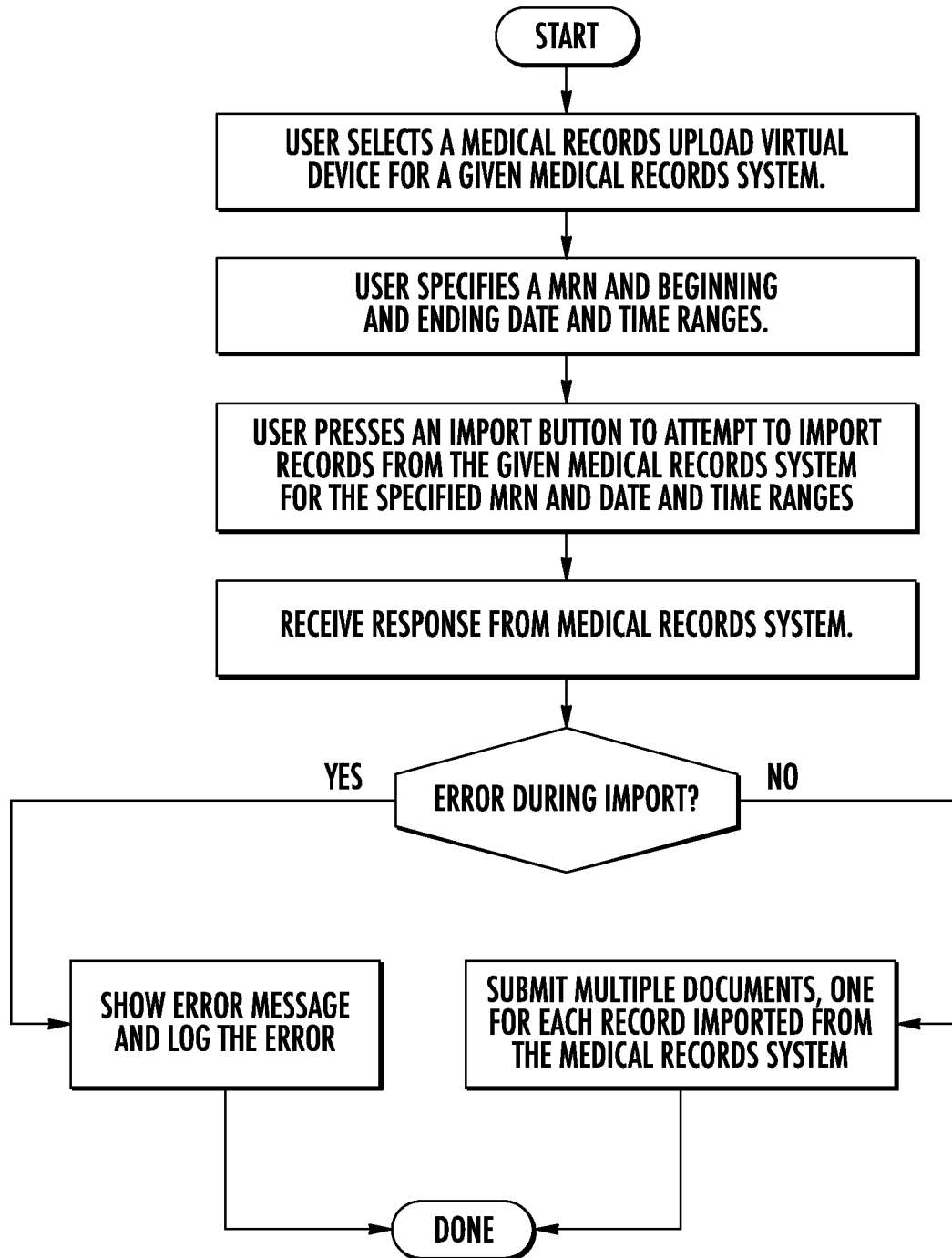
FIG. 8 is a flowchart illustrating a method of uploading or importing patient medical information/records according to an embodiment.

FIG. 8 shows virtual devices, which are devices that are implemented purely in software. The inclusion of virtual devices allows novel workflows such as setting predefined documents that can be submitted at the press of a button for common functions (e.g., sending a note indicating that the patient's eyes were dilated), creating devices that import data from existing medical records systems, or using a smartphone to capture and submit data). The medical records import virtual device allows a user to import existing medical record data from various medical records systems, and then upload those records as Documents and link them to a patient's Session. The user would select the medical records system to import from, provide an MRN, time and date range, and any other search criteria specific to the selected medical records system. The medical records import virtual device would then connect to the medical records system, and import as Documents any records that match the specified search criteria.

Figure 10:
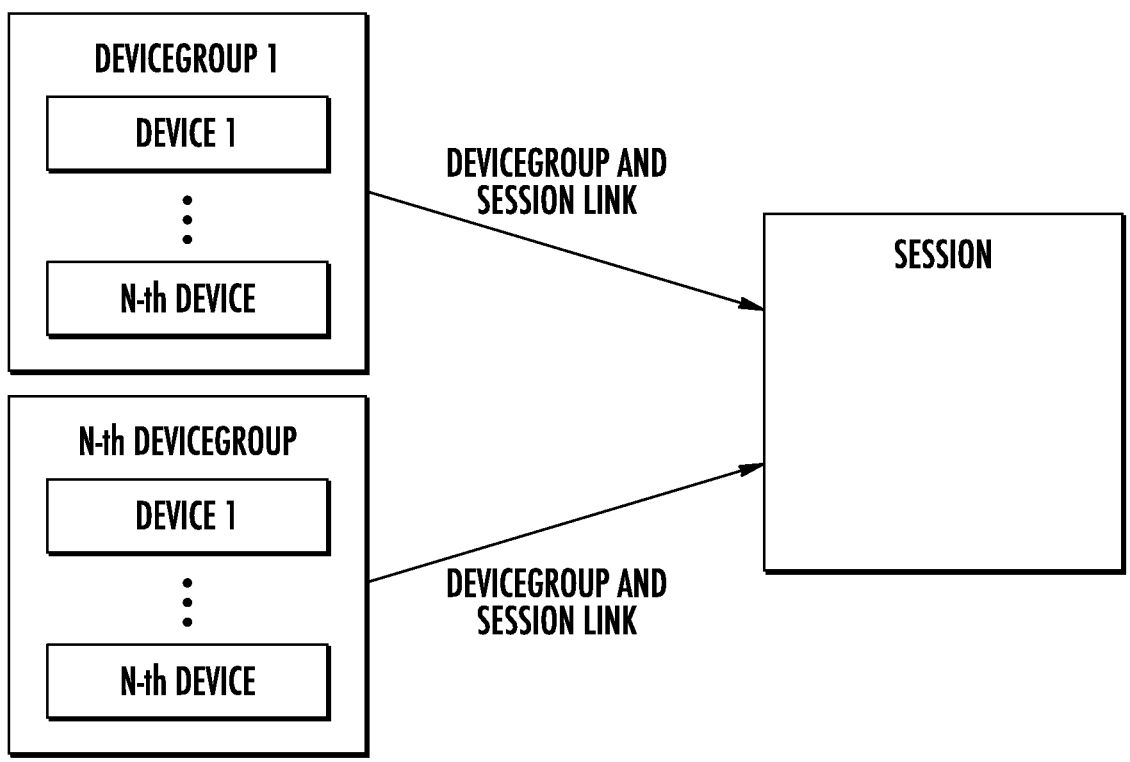
FIG. 10 is a block diagram illustrating a relationship between Devices associated to Session via DeviceGroup according to an embodiment.
Figure 11:
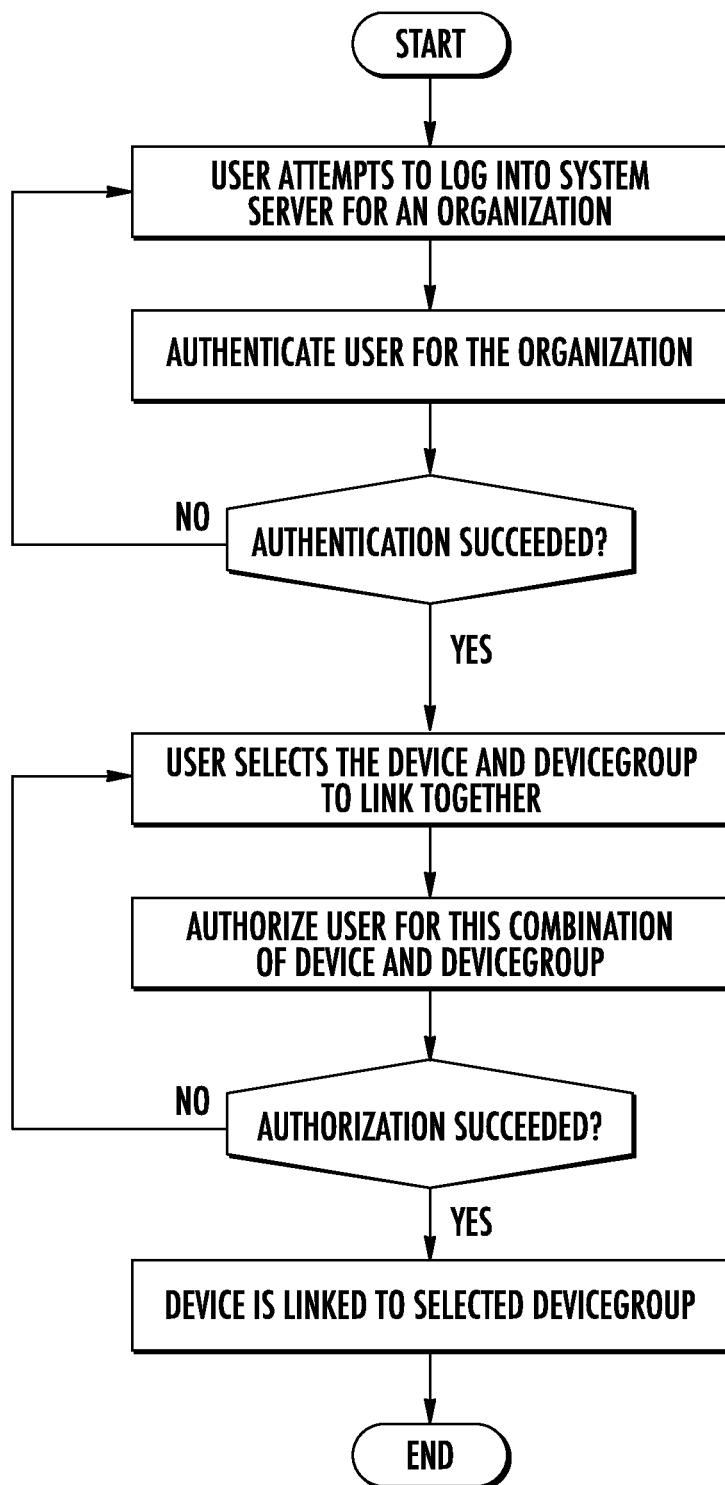
FIG. 11 is a flowchart illustrating a method of user authentication and linking a device or device group to a medical examination session according to an embodiment.

FIG. 10 shows devices or device groups (DEVICEGROUP) associated to a medical examination session (SESSION) via a device or device group, for example. It shows how devices are, in certain embodiments, contained within device groups, and the device groups are linked to medical examination sessions. This structure allows a device to submit medical data without any knowledge of the patient for whom it is submitting data. This is an important distinction since it allows medical data to be submitted without also submitting any personally identifiable data along with it. It also illustrates validation of the device or device group based on credentials of, for example, a user.

EXAMPLES

Example 1

In an embodiment, there will be a centralized repository for medical data using a common format. For example, the atomic unit of data is the Document. These represent one data capture event, but can contain multiple data blocks. In aspects, each data block is a Page, and has standard metadata associated with it (e.g., type), binary data (e.g., the actual measurement), and user defined custom metadata. The Document(s) may have one or more Pages. In aspects, Documents are grouped into Sessions, which represent a medical encounter session of a patient with a physician, by way of example.

In an embodiment, Devices do not have any knowledge of the Sessions they are associated with; they send data to a central service, and that service is responsible for attaching the Documents sent by the Device to the correct Session. If a Device is not associated with a Session, then the Documents are left unassociated, and will need to be manually attached, for example.

In aspects, Devices are grouped together into DeviceGroup collections. These collections may be defined by a user or pre-defined. In aspects, DeviceGroup(s) represent all Devices in a room, office, hospital, or other location, all Devices of a given type, or all Devices in an entire organization. A purpose of a DeviceGroup, other than organization, is to associate Devices with Sessions. Devices in a DeviceGroup may be associated with a Session that the DeviceGroup is attached to; for example, when all Devices are in a single exam room. In an example, a single patient will be in an exam room, so all Devices in that room should send their Documents to the Session for that patient.

Example 2

In an embodiment, when a Device submits a Document tagged with the Device's ID, it connects to a remote service and sends the contents of the Document as a serialized payload (e.g., Document is converted to a Javascript Object Notation strife for transport). Transport level security is required to ensure that the Document is encrypted as it is transmitted. One example of transport level security is HTTPS (hypertext transfer protocol secure) as the transport protocol.

When the remote service receives the Document, the medical data is read from the Document, encrypted, and stored in a secure location. The medical data is then removed from the Document so that it is not stored along with the Document's metadata in the database. The Device II) is read from the Document. An attempt to load the Session associated with the Device's DeviceGroup from the database is performed. If no associated Session is found, the Document is put into a special "Unassociated Devices" Session and a success response is sent back to the Device indicating that the Document was received. If a Session is found, the Document is attached to that Session's Documents list, and a success response is sent back to the Device indicating that the Document was received. All data in the database may be encrypted at rest.

Example 3

In an embodiment, Devices will submit Documents into a "Received Documents" queue, and a success response will immediately be returned to the Device to indicate reception, but not processing, of the Document. Decoupling Document upload from Document processing allows the Document processing to occur horizontally by spinning up more Document processors. In aspects, a mirrored Document queue may be implemented to allow testing staged updates. Audits can be attached to the queues.

A service can read Documents from the "Received Documents" queue and spawn worker processes to process the Documents. Each worker process can follow the current steps to do basic processing of the Documents. Upon completion, the worker process will post a new message to a "Documents Processed" queue. Any services watching the "Documents Processed" queue will respond to the new "Processed" message. This allows for secondary processing of the data without impacting the main workflow. Examples of secondary processes include, but are not limited to: generate thumbnails; convert Document Page binary data into various industry standard formats and attach the converted data as new Pages in the original Document; upload the Document data to an Medical Records application; and/or send notifications.

Embodiments of the invention also include a computer readable medium comprising one or more computer files comprising a set of computer-executable instructions for performing one or more of the calculations, steps, processes and operations described and/or depicted herein. In exemplary embodiments, the files may be stored contiguously or non-contiguously on the computer-readable medium. Embodiments may include a computer program product comprising the computer files, either in the form of the computer-readable medium comprising the computer files and, optionally, made available to a consumer through packaging, or alternatively made available to a consumer through electronic distribution. As used in the context of this specification, a "computer-readable medium" is a non-transitory computer-readable medium and includes any kind of computer memory such as floppy disks, conventional hard disks, CD-ROM, Flash ROM, non-volatile ROM, electrically erasable programmable read-only memory (EEPROM), and RAM. In exemplary embodiments, the computer readable medium has a set of instructions stored thereon which, when executed by a processor, cause the processor to perform tasks, based on data stored in the electronic database or memory described herein. The processor may implement this process through any of the procedures discussed in this disclosure or through any equivalent procedure.

In other embodiments of the invention, files comprising the set of computer-executable instructions may be stored in computer-readable memory on a single computer or distributed across multiple computers. A skilled artisan will further appreciate, in light of this disclosure, how the invention can be implemented, in addition to software, using hardware or firmware. As such, as used herein, the operations of the invention can be implemented in a system comprising a combination of software, hardware, or firmware.

Embodiments of this disclosure include one or more computers or devices loaded with a set of the computer-executable instructions described herein. The computers or devices may be a general purpose computer, a special-purpose computer, or other programmable data processing apparatus to produce a particular machine, such that the one or more computers or devices are instructed and configured to carry out the calculations, processes, steps, operations, algorithms, statistical methods, formulas, or computational routines of this disclosure. The computer or device performing the specified calculations, processes, steps, operations, algorithms, statistical methods, formulas, or computational routines of this disclosure may comprise at least one processing element such as a central processing unit (i.e., processor) and a form of computer-readable memory which may include random-access memory (RAM) or read-only memory (ROM). The computer-executable instructions can be embedded in computer hardware or stored in the computer-readable memory such that the computer or device may be directed to perform one or more of the calculations, steps, processes and operations depicted and/or described herein.

Additional embodiments of this disclosure comprise a computer system for carrying out the computer-implemented method of this disclosure. The computer system may comprise a processor for executing the computer-executable instructions, one or more electronic databases containing the data or information described herein, an input/output interface or user interface, and a set of instructions (e.g., software) for carrying out the method. The computer system can include a stand-alone computer, such as a desktop computer, a portable computer, such as a tablet, laptop, PDA, or smartphone, or a set of computers connected through a network including a client-server configuration and one or more database servers. The network may use any suitable network protocol, including IP, UDP, or ICMP, and may be any suitable wired or wireless network including any local area network, wide area network, Internet network, telecommunications network, Wi-Fi enabled network, or Bluetooth enabled network. In one embodiment, the computer system comprises a central computer connected to the internet that has the computer-executable instructions stored in memory that is operably connected to an internal electronic database. The central computer may perform the computer-implemented method based on input and commands received from remote computers through the internet. The central computer may effectively serve as a server and the remote computers may serve as client computers such that the server-client relationship is established, and the client computers issue queries or receive output from the server over a network.

The input/output interfaces may include a graphical user interface (GUI), which may be used in conjunction with the computer-executable code and electronic databases. The graphical user interface may allow a user to perform these tasks through the use of text fields, check boxes, pull-downs, command buttons, and the like. A skilled artisan will appreciate how such graphical features may be implemented for performing the tasks of this disclosure. The user interface may optionally be accessible through a computer connected to the internet. In one embodiment, the user interface is accessible by typing in an internet address through an industry standard web browser and logging into a web page. The user interface may then be operated through a remote computer (client computer) accessing the web page and transmitting queries or receiving output from a server through a network connection. Additionally, and as previously discussed above, in aspects, the system and method will allow the user to interact with it using other interfaces other than traditional keyboard-, mouse-, touchpad-, stylus-, or screen-based interfaces, such as, but not limited to, foot pedals, physical buttons, haptic feedback, or projected interface elements, and may include multiple interface options in combination with one another, to allow maximum flexibility in the ways the user can interact with the system in recognized ways that will minimize breaks in clinical workflow and non-ergonomic system engagements.

One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context dearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. A method of managing coordination of information related to a medical examination, comprising:
    Analyzing user credentials and authenticating access to a premises or a device or device group based on the user credentials;
    Validating use of the device or device group based on the user credentials and the type of device or device group;
    Associating a medical examination with a patient or patients or a medical examination schedule;
    Associating medical examination data and/or metadata from one or more device or device group with a related medical examination session;
    Routing medical examination data and/or metadata to a local and/or external computer database or databases;
    Pairing the medical examination session and/or medical examination data and/or metadata with a manual or automated medical interpretation, results, diagnosis or diagnoses, and/or recorded information from the medical examination; and
    Allowing the user to authenticate or sign the manual or automated medical interpretation, results, diagnosis or diagnoses, and/or recorded information from the medical examination, wherein the manual or automated medical interpretation, results, diagnosis or diagnoses, and/or recorded information from the medical examination is displayed to the user, wherein the user indicates a review and/or an approval or rejection of the manual or automated medical interpretation, results, diagnosis or diagnoses, and/or recorded information from the medical examination, and/or wherein the user indicates signing or delaying signature of the medical examination, the medical examination data and/or metadata, and/or the manual or automated medical interpretation, results, diagnosis or diagnoses, and/or recorded information from the medical examination.

2. A method of managing coordination of information related to a medical examination according to claim 1, wherein the medical examination schedule is correlated with time of use of the device or device group, physical location or physical locations of the user or the device or device group, physical location or physical locations of a compatible device or a compatible device group, electronic medical record or electronic scheduling software, and/or manual or automated schedules.

3. A method of managing coordination of information related to a medical examination according to claim 1, wherein the location or locations and/or identity of the user or users of the device or device group is determined by geolocation, physical tokens, virtual tokens, software-based tokens, passcode, QR codes, bar codes, identification cards, encoded magnetic or solid-state electronic memory cards and/or compatible wireless antennas and solid state computing chips, Near Field Communication cards, Wi-Fi pairing, Bluetooth or ZigBee pairing, radio beacons, paired and authenticated mobile devices, Radio Frequency Identification tags or sensors, manual entry of the location or locations, detection of wired or wireless beacon, biometric identification techniques, Internet Protocol and/or Media Access Control address of the device or device group, scanning of the user or the device or device group, passcodes, and/or software applications.

4. A method of managing coordination of information related to a medical examination according to claim 1, further comprising associating telemetry data from the medical device or device group with the medical examination session.

5. A method of managing coordination of information related to a medical examination according to claim 1, wherein the medical examination data and/or metadata comprises information collected by the device or device group by the user during the medical examination session.

6. A method of managing coordination of information related to a medical examination according to claim 1, wherein associating the medical examination data and/or metadata from one or more medical device or device group with a related medical examination session comprises:

Retrieving information related to the medical examination schedule, the patient or patients, the device or device group, the user, and/or a location of the device or device group and associating that information with the medical examination session; and Associating the medical examination data and/or metadata with the medical examination schedule, a corresponding patient appointment time, and/or the medical examination session.

7. A method of managing coordination of information related to a medical examination according to claim 1, further comprising retrieving medical data of the patient or patients from one or more medical record or one or more medical database and/or sending medical data of the patient or patients recorded during the medical examination session.

8. A method of managing coordination of information related to a medical examination according to claim 7, wherein the user has full or partial access to medical data of the patient or patients depending on the user's credentials.

9. A method of managing coordination of information related to a medical examination according to claim 1, wherein routing medical examination data and/or metadata to a local and/or external computer database or databases is conducted via a coordinating service application.

10. A method of managing coordination of information related to a medical examination according to claim 9, wherein the coordinating service application is hosted on a host of servers or a distributed cloud service which is remotely located.

11. A method of managing coordination of information related to a medical examination according to claim 9, wherein the coordinating service application is hosted on a centralized server located locally to the device or device group.

12. A method of managing coordination of information related to a medical examination according to claim 1, further comprising recording and/or tracking an audit trail record of one or more user, use of a device or device group, and/or who or what is accessing data and/or metadata related to the medical examination session or the patient record.

13. A method of managing coordination of information related to a medical examination according to claim 1, further comprising generating documentation based on some or all of the medical examination data and/or metadata, and/or some or all of the manual or automated medical interpretation, results, diagnosis or diagnoses, and/or recorded information from the medical examination.

14. A method of managing coordination of information related to a medical examination according to claim 1, further comprising generating categories or formats of documentation for different or varying purposes including billing, medical charting, research, quality improvement, and/or backup based on data and/or metadata generated by the device or device group and/or the manual or automated medical interpretation, results, diagnosis or diagnoses, and/or recorded information from the medical examination.

15. A method of managing coordination of information related to a medical examination according to claim 1, further comprising processing the medical examination data and/or metadata by cross-referencing with other medical information to aid in diagnosis.

16. A method of managing coordination of information related to a medical examination according to claim 1, further comprising processing of data and/or metadata from the user, the patient or patients, and/or the device or device group to analyze and report clinical association or associations and/or finding or findings to aid in diagnosis, treatment, and/or management of the patient or patients.

17. A method of managing coordination of information related to a medical examination according to claim 1, wherein the data and/or metadata from the user, the patient or patients, and/or the device or device group is sent to an external computing device or database for automated diagnoses, treatment, and/or management information for the patient or patients.

18. A method of managing coordination of information related to a medical examination according to claim 1, further comprising displaying information related to the medical examination session to the user, the patient or patients, medical professional or medical professionals, and/or local or remote electronic device.

19. A method of managing coordination of information related to a medical examination according to claim 1, further comprising allowing electronic signature, authentication, validation, rejection, delaying, and/or review of generated documents and reports using a physical device, virtual device, an electronic device, a computing device, and/or a mobile device.

20. A method of managing coordination of information related to a medical examination according to claim 1, further comprising uploading telemetry and/or metadata from the device or device group to store, authenticate, and/or validate telemetry and/or metadata associated with the device or device group.

21. A method of managing coordination of information related to a medical examination according to claim 1, further comprising linking telemetry and/or metadata from the device or device group with the medical examination session.

22. A method of managing coordination of information related to a medical examination according to claim 1, further comprising allowing automation of certain functions of the device or device group, including setting predefined parameters, synchronizing, importing or exporting information, and/or using an external electronic device to send or retrieve information.

23. A method of managing coordination of information related to a medical examination according to claim 1, further comprising providing the user an indication whether manual data entry tasks are required for validation, authentication, uploading, downloading, managing clinical inventory, sending, receiving, and/or recording.

24. A method of managing coordination of information related to a medical examination according to claim 1, further comprising using device or device group or system telemetry and/or metadata to automatically and/or interactively generate clinical practice metrics and reports.

* * * * *